(12) United States Patent
Thorne, Jr. et al.

(10) Patent No.: US 9,950,114 B2
(45) Date of Patent: Apr. 24, 2018

(54) DUAL-CHAMBER SYRINGE AND ASSOCIATED CONNECTING SYSTEMS

(71) Applicant: Thorne Consulting and Intellectual Property, LLC, Bountiful, UT (US)

(72) Inventors: Gale Harrison Thorne, Jr., Bountiful, UT (US); Kendall Patterick Thorne, Layton, UT (US); Gale Harrison Thorne, Bountiful, UT (US)

(73) Assignee: THORNE CONSULTING FOR INTERNATIONAL PROPERTY, LLC, Bountiful, UT (US)

( * ) Notice: Subject to any disclaimer, the term of this patent is extended or adjusted under 35 U.S.C. 154(b) by 333 days.

(21) Appl. No.: 14/921,343

(22) Filed: Oct. 23, 2015

(65) Prior Publication Data
US 2016/0175537 A1    Jun. 23, 2016

Related U.S. Application Data

(63) Continuation-in-part of application No. 14/121,681, filed on Oct. 7, 2014, which is a continuation-in-part
(Continued)

(51) Int. Cl.
*A61M 5/00* (2006.01)
*A61M 5/19* (2006.01)
(Continued)

(52) U.S. Cl.
CPC .............. *A61M 5/19* (2013.01); *A61M 5/002* (2013.01); *A61M 5/3129* (2013.01);
(Continued)

(58) Field of Classification Search
CPC .. A61M 2005/3125; A61M 2005/3126; A61M 5/19; A61M 2005/1787; A61M 5/31596; A61M 2005/31598
See application file for complete search history.

(56) References Cited

U.S. PATENT DOCUMENTS 2,939,459 A * 6/1960 Lazarte ............. A61M 5/31596
604/191
3,477,432 A * 11/1969 Shaw ................ A61M 5/31596
604/91
(Continued)

*Primary Examiner* — Kami A Bosworth
*Assistant Examiner* — William Carpenter
(74) *Attorney, Agent, or Firm* — Gale H. Thorne

(57) ABSTRACT

A dual-chamber syringe system is disclosed. Critical system oriented elements are disclosed, including plunger valve designs for accurate measurement and true, non-canting displacement; tamper and inadvertent valve actuation indicators, as well as, valve status indicators; anti-reflux construction; novel indicia patterns for dual-chamber syringe operation; structure and method for quality assurance that no gas can be delivered from a proximal chamber of the dual-chamber syringe and a kit for single step dose transfer. In addition, a tapered fitting valve is disclosed. The tapered fitting valve comprises a single molded incompressible, but supple part and a skeletal support whereby the tapered fitting valve is opened by insertion into a tapered fitting. The preferred embodiment of an actuator portion of the valve is elliptical in shape. The valve opens by compressing a slit which is parallel to, but offset from the major elliptical axis to provide sufficient space for other valve components within a limited size, such as that of a luer fitting. A syringe barrel comprising a skeletal support structure for an affixed valve for a tapered fitting is also disclosed.

10 Claims, 9 Drawing Sheets

Related U.S. Application Data of application No. 13/872,828, filed on Apr. 29, 2013, now Pat. No. 9,295,827, and a continuation-in-part of application No. 13/068,529, filed on May 13, 2011, now Pat. No. 9,289,562.

(51) Int. Cl.

| | |
|---|---|
| *A61M 5/315* | (2006.01) |
| *A61M 5/31* | (2006.01) |
| *A61M 5/50* | (2006.01) |
| *A61M 5/36* | (2006.01) |
| *F16K 15/14* | (2006.01) |
| *A61M 5/178* | (2006.01) |
| *A61M 39/24* | (2006.01) |

(52) U.S. Cl.
CPC .... *A61M 5/31501* (2013.01); *A61M 5/31511* (2013.01); *A61M 5/31596* (2013.01); *A61M 5/365* (2013.01); *A61M 5/5086* (2013.01); *F16K 15/147* (2013.01); *A61M 2005/1787* (2013.01); *A61M 2005/3114* (2013.01); *A61M 2005/3121* (2013.01); *A61M 2005/3125* (2013.01); *A61M 2039/2426* (2013.01)

(56) References Cited

U.S. PATENT DOCUMENTS

| | | | | |
|---|---|---|---|---|
| 5,429,610 | A * | 7/1995 | Vaillancourt | A61M 5/31596 600/573 |
| 5,743,886 | A | 4/1998 | Lynn et al. | |
| 7,048,720 | B1 | 5/2006 | Thorne, Jr. et al. | |
| 7,101,354 | B2 | 9/2006 | Thorne, Jr. et al. | |
| 7,766,304 | B2 | 8/2010 | Phillips | |
| 7,789,862 | B2 * | 9/2010 | Thorne, Jr. | A61M 5/284 604/190 |
| 7,803,140 | B2 | 9/2010 | Fangrow | |
| 7,938,805 | B2 | 5/2011 | Harding et al. | |
| 2008/0208137 | A1 * | 8/2008 | Fago | A61M 5/31596 604/191 |
| 2012/0265171 | A1 * | 10/2012 | Thorne, Jr. | A61M 5/31596 604/518 |
| 2012/0323173 | A1 * | 12/2012 | Thorne, Jr. | A61M 5/31596 604/89 |
| 2014/0207079 | A1 * | 7/2014 | Creaturo | A61M 5/002 604/207 |
| 2015/0032063 | A1 * | 1/2015 | Thorne | A61M 5/31596 604/207 |
| 2016/0166776 | A1 * | 6/2016 | Appelbaum | A61M 5/31525 604/189 |

* cited by examiner

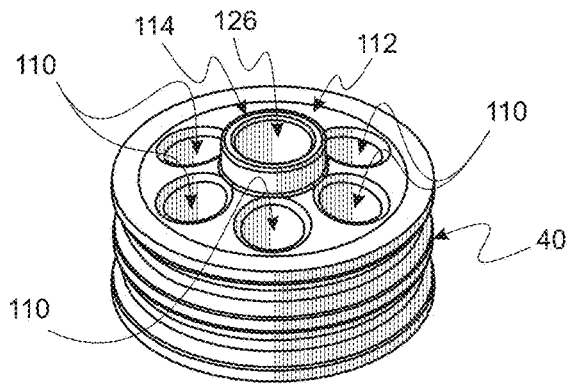
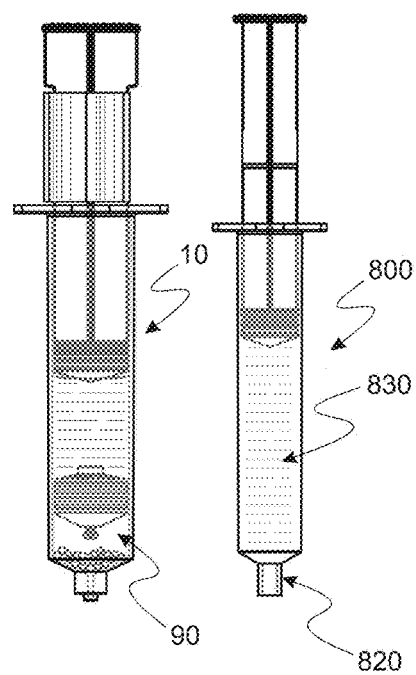
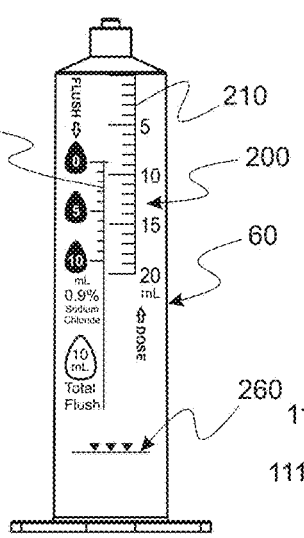
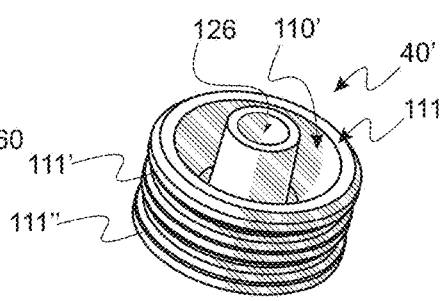
FIGURE 3
FIGURE 36
FIGURE 13   FIGURE 12   FIGURE 3A

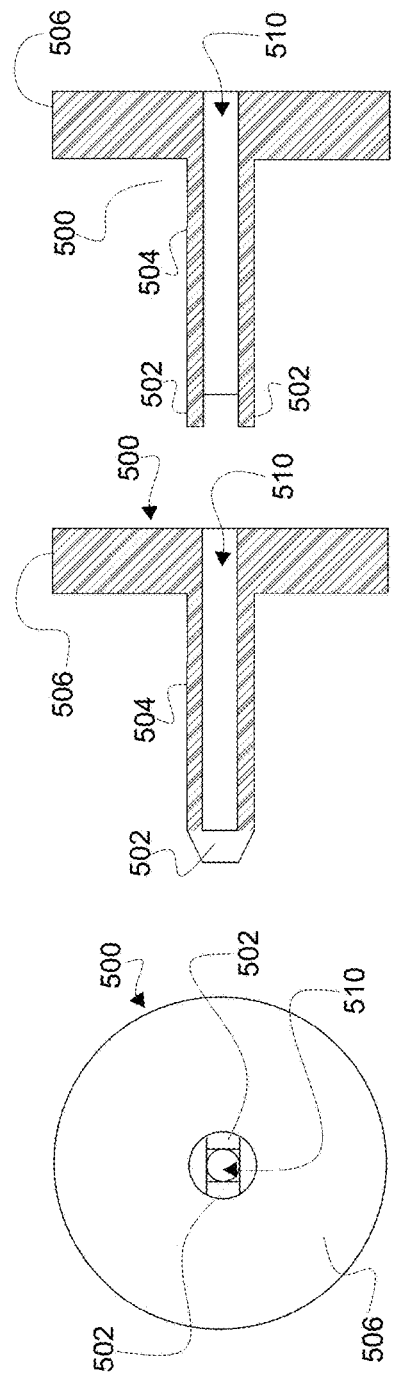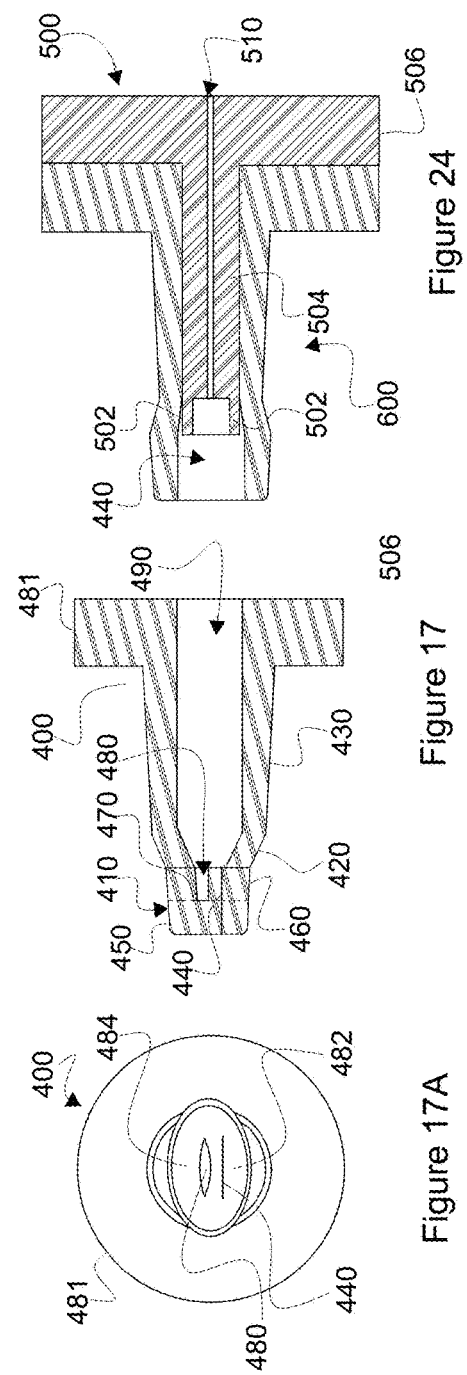

DUAL-CHAMBER SYRINGE AND ASSOCIATED CONNECTING SYSTEMS

CONTINUITY

This application is a Continuation-in-Part of U.S. patent application Ser. No. 14/121,681 filed Oct. 7, 2014 and titled COMPONENTS AND DEVICES FOR CLOSED MEDICAL SYSTEM OPERATION by Gale H. Thorne (referenced hereafter as Thorne 681) which is a Continuation-in-Part of U.S. patent application Ser. No. 13/872,828, filed Apr. 29, 2013 and titled TWISTED SLIT VALVE filed by Gale H. Thorne (referenced hereafter as Thorne 828) and, further, a Continuation-in-Part of U.S. patent application Ser. No. 13/068,529 filed May 13, 2011 by Gale H. Thorne, et al. and titled PRESSURE ACTUATED VALVE FOR MULTI-CHAMBER SYRINGE APPLICATIONS (hereafter referenced as Thorne 529), contents of each of which are made part hereof, by reference.

FIELD OF INVENTION

This application relates to dual-chamber syringes and more particular to syringes having conventional barrels of substantially constant diameter divided into two chambers by one or more plunger valves which are normally closed and selectively opened to dispense liquids from a more proximal chamber distally. Preferably, syringes used within the scope of the instant inventions comprise conventional barrels of consistent diameter along the length of such. Further, this application relates to novel valves for tapered fittings and methods which are formulated to improve efficacy and safety of dual-chamber syringes in medical practice.

BACKGROUND

Disclosures of U.S. Pat. No. 7,789,862 issued to Gale H. Thorne, Jr. et al. Sep. 7, 2010, and other related U.S. Patent Applications describe separating a conventional syringe barrel into two chambers via a plunger valve having a displaceable stem. However, none of the disclosures treat critical system factors associated with placing a dual-chamber syringe system in commerce. Not only is a dual-chamber syringe required to keep fluids in each chamber of the syringe disparate and deliver only liquid chamber contents sequentially, but other concerns and factors must be considered to make a dual-chamber syringe system viable. A number of system responses to those concerns and factors yield novel methods and devices as part of the system disclosure disclosed herein.

As disclosed in referenced U.S. Patent Applications from which this disclosure continues, dual-chamber syringes commonly comprise a plunger valve which is normally closed and selectively opened for transmitting fluids from a disparate chamber within the syringe. However, in medical practice, dual-chamber device efficacy and safety requires more to be considered than simply the valve and valve actuation alone, although the valve and selective chamber disparateness are critical parameters. As a system, the following operational parameters should be duly considered:

1. accuracy of measurement of dispensed dose
2. a tamper-evident indicator to provide assurance that system is ready
3. certainty of valve actuation only at a desired point in a medical procedure
4. assurance that no back-flow or reflux occurs as dispensing is completed
5. indicia provided upon the barrel of the syringe clearly depicts needed information and is neither confusing nor perplexing
6. monitoring of critical safety parameters
7. compatibility with preferred sterilization procedure
8. number of fluid transfer steps required to fill or mix liquids in a distal chamber
9. closed system operation when handling hazardous or air sensitive materials Safety and efficacy of dual-chamber syringe operation is as much dependent upon the above considerations as a properly operating plunger valve. Such parameters may require different parameter considerations for different modes of plunger valve actuation as is disclosed in detail hereafter.

Measurement Accuracy

With a properly operating plunger valve, there are two conditions which affect measurement accuracy. The first is assurance that all fluid is expelled from a first dispensing chamber before an associated plunger valve is opened to dispense fluid from a second chamber. The second is more critical, because, in conventional syringe operation, measurement of successive volume dispensed is communicated from a plunger through a barrel having indicia marked to measure plunger displacement. As a plunger in a dual-chamber syringe is not mechanically affixed to a stabilizing stem and is, therefore, displaced only by force of fluid within a syringe barrel and variously retarded by internal barrel friction, it is critical that the plunger displacement be "true" and that the plunger not cant during displacement because such canting, though insufficient to permit fluid flow between chambers, could result in inaccurate volumetric measurement due to linear angular displacement of the plunger valve to barrel alignment.

Tamper Evidence

Improper handling of a dual-chamber syringe device can actuate a valve prematurely, resulting in untimely mixing of dose chamber fluid with fluid in a proximal chamber. A tamper evident indicator would preclude using a syringe having such a problem.

Valve Actuation

A plunger valve, opened by displacement of an associated stem, can be inadvertently actuated by inadvertent undue displacement of the plunger valve during a filling process. As stated supra, premature valve actuation can result in mixing of fluids which should otherwise remain disparate. It is also desirable for a clinician to know when a drug dose has been delivered and a following delivery of a flushing liquid has begun.

Reflux

Dual-chamber syringes provide a unique opportunity for reflux occurring not at the end of delivery of fluid from a first of distal chamber, but upon final delivery from the upstream or more proximal chamber. Such reflux may be somewhat curtailed by pressurized air remaining in the proximal chamber, but, more likely, slower to recover compression of elastic members associated with the proximal chamber can result in a negative pressure relative to downstream fluids and resultant reflux. Such reflux is highly undesirable in patient catheter lines and in other applications where retrograde flow can cause blockage. In U.S. Pat. No. 7,789,862 reflux is taught to be assuaged by gas pressure resident in a rear chamber upon final dispensing of liquid therefrom. However, careful analysis of dynamics of actions which generate reflux show that pressure reduction in the rear chamber occurs too rapidly when compared to reflux producing mechanical structure within the chamber to effectively arrest all reflux.

Indicia

Measurement indicia must clearly provide for not only distal chamber volumetric determinations, but for accurate proximal chamber determinations, as well. Further, because of the likelihood of the proximal chamber being pre-filled, volumetric and other identifying indicia are also needed. Because there are two plungers in a dual-chamber syringe and two associated chambers for which volumes should be accurately measured, a number of indicia patterns are possible. Some of the possibilities place special requirements on filling and other factors such as a maximum volume of gas which can be stored in a proximal chamber.

Safety Monitoring

It is standard practice to purge all gas from a syringe prior to dispensing liquid therefrom. While such can be accomplished in a single (conventional) syringe, a dual-chamber syringe may have gas disposed in the proximal chamber due to filling procedures or outgassing. Of course, a plunger valve for a dual-chamber syringe should be designed to separate gas from liquid for a liquid only delivery, such as provided by a liquid only zone device. However, for quality assurance purposes, a control check should be provided for both manufacturing and user testing.

Sterilization Procedure Compatibility

Presently preferred sterilization of pre-filled syringes is by gamma radiation. For this reason all materials, particularly those which are used to form the syringe barrel, valve plunger and stem and plunger and plunger rod, should be selected to be unaffected or at least predictably affected and not operationally impaired thereby.

Fluid Transfer Methods and Apparatus

In such applications as PIXUS storage and retrieval, a system comprising a dual-chamber syringe may profitably enclose both a dual-chamber syringe and an associated distal chamber fluid containing vessel in the same package. Conventionally, if both the syringe and vessel comprise male luer fittings, a female/female luer connector is employed. However, introduction of an additional component adds steps and introduces further opportunity for contamination.

Closed System Operation

There are many reasons for keeping a system closed during a medical procedure (e.g. handling hazardous drugs or air sensitive materials). A male luer fitting of a medical syringe is inherently open when disconnected from a female fitting. For this reason, needleless connectors and male adapters are commonly employed in oncology drug delivery. However, as considered for Fluid Transfer, supra, such generally requires additional components, steps and associated cost.

General

While the above disclosed considerations apply generally to dual-chamber syringes, it is considered prudent to provide an opportunity for evaluating these considerations across a spectrum of dual-chamber syringe designs. In addition, a syringe having structure for an integrally affixed tapered valve is also provided.

Definitions for Terms Used assembly n: a device which is made from at least two interconnected parts barrel n: a cylindrical elongated portion of a conventional syringe which is substantially of constant diameter along a long axis of the syringe, open on one end to receive a plunger tip and plunger rod assembly used for displacing fluid within the barrel and partially closed at an opposite end except for an orifice or portal through which fluid is ejected or aspirated chamber n: a disparate volumetric portion of a divided barrel conventional adj: sanctioned by general custom; i.e. commonplace, ordinary disparate n: when used to describe a first volume of contents relative to another volume of contents, the first volume of contents being kept distinctly separate from the other volume of contents differential pressure ($\Delta P$) n: a pressure gradient resulting from unequal pressures exerted upon opposing sides of a structure; generally as used herein, $\Delta P = P_p - P_d$, where subscript "p" represents proximal and subscript "d" represents distal.

distal adj: a term which depicts placement away from a reference point (e.g. away from a user of a syringe)

downstream adj: a direction which is consistent with flow out of a syringe or away from a user fluid n: a substance (e.g. a liquid or gas) which tends to take the shape of a container front adj/n: when referenced to a syringe, a distally disposed or a distally disposed site (e.g. a front of a syringe comprises the commonly provided luer fitting and associated orifice)

gas n: a fluid which is neither solid nor liquid liquid n: a fluid which is neither solid nor gaseous, free flowing like water liquid only zone n: a space within a syringe barrel which can only be physically occupied by liquid (see Thorne 862)

medial adj: occurring away from an outer edge; disposed near the center of (e.g. disposed away from an edge or periphery and in the vicinity of a center of gravity or axis of symmetry)

plunger rod n: a portion of a syringe piston apparatus, usually affixed to a plunger tip, to which force is applied to displace fluid within a syringe barrel plunger n: a portion of a part that divides a syringe barrel into two disparate fore and aft chambers.

prime v: to completely fill liquid into a cavity generally by removing air therefrom (e.g. priming a gas separator)

proximal adj: opposite of distal (e.g. a term which depicts placement nearer to a reference point)

rear adj: opposite from front (i.e. generally associated with a part of a syringe barrel which is proximal to a syringe user relative to an outflow orifice)

reflux n: a type of retrograde (upstream) flow relative to a direction of dispensing, usually resulting from energy stored in flow-producing parts of a syringe and usually undesired state n: a mode or condition of matter, e.g. gaseous, liquid or solid or of a device, such as an open state of a valve stiction n: a special case of friction; stiction being related to the force required to initiate motion to a resting body, esp. when that force is greater than friction associated with a moving body stop n: an obstruction which is differentiated from friction or stiction which halts displacement of a stopper or plunger without retrograde motion stopper n: a plug substantially adv: to a most reasonably achievable amount syringe n: a medical device used for injecting or withdrawing fluids, a syringe usually comprising a plunger and plunger rod disposed to be displaced within a conventional cylindrical syringe barrel and, for a dual-chamber syringe, includes a plunger valve to provide the dual-chamber syringe

BRIEF SUMMARY AND OBJECTS OF THE INVENTION

In brief summary, the novel inventions disclosed herein, while having broader applications, alleviates known problems related to providing commercially viable dual-chamber syringe systems. Dual-chamber syringes for such systems preferably comprise a conventional syringe barrel having a substantially uniform internal cylindrical barrel divided into two disparate chambers (proximal and distal) by a plunger valve, which is normally closed. In particular, as an example of a dual-chamber syringe for such systems, such a syringe comprises a plunger valve having a stem which is displaced by collision with the distal end of the syringe following a distal chamber dispensing cycle. The collision opens the valve for disparately dispensing contents from the proximal chamber. It should be recognized that gas can be discharged from the distal chamber in the manner generally employed in conventional syringe use. Any gas residing in the proximal chamber is trapped and retained therein such that no gas is delivered from the proximal chamber. The following summary is organized to provide disclosure of novel methods and apparatus which provide solutions for problems listed for the operational parameters cited above:

Accuracy of Measurement of Dispensed Dose

In conventional syringe use, metering of a dispensed or drawn dose is dependent upon visually interrelating the distal edge of a plunger with indicia on the exterior of a syringe barrel. It is well known in medical syringe art that canting of a plunger results in misalignment between plunger edge and indicia lines making measurement less accurate. In conventional syringes, canting is impeded by plunger rod to plunger assembly structure. However, an unattached fluid driven plunger, such as the chamber separating plunger in a dual-chamber syringe, must be canting free for other reasons.

A ring (306), proximally disposed in a plunger valve to obviate canting, is disclosed in U.S. Pat. No. 7,789,862. However, a ring is a separate part which adds to the overall cost of the dual-chamber syringe in which it is employed. A novel approach as part of the instant invention comprises structure within the proximal part of the plunger valve which provides sufficient space for gas capture and retention while providing suitable support for the proximal portion of the valve to retard canting. In the preferred embodiment, the support is afforded by a plurality of joined tubes which communicate the support to the circumference of the valve while providing a necessary volume for gas capacity. In addition to resisting canting, such rear support also precludes departure of outer cylindrical portions of the associated plunger from the inner surface of the barrel which would otherwise result in liquid communicating within the plunger to barrel interface, a condition which is highly undesirable.

Tamper-Evident Indication

Tamper evidence is generally provided as a visual indicator. The greatest effect of operational tampering in a dual-chamber syringe is premature actuation of an associated plunger valve. To make actuation more evident, only a portion of an associated plunger valve stem is visibly seen on the distal side of a non-actuated plunger valve and only an extended end of the stem is seen on the proximal end of an actuated valve. While this is noticeable as a tamper-evident indicator, it is also an indicator of proper valve switching during a liquid dispensing procedure.

Reflux Inhibition

Generally reflux in a medical line (such as a catheter) is the consequence of upstream directed flow resulting from compression followed by relaxation of elastic parts, generally at the end of a delivery cycle of fluid from a proximal chamber of the dual-chamber syringe. Of course, one skilled in catheter delivery art understands that such upstream flow brings body fluids into the line which is generally negatively consequential.

In a dual-chamber syringe system involving a displaceable syringe stem for opening a fluid conduit to a liquid only zone, two novel approaches provide assurance against reflux. In a first approach, a stem having a length and geometry which provides for resetting the stem to close the valve and conduit pathway from the liquid only zone is effective in stopping further reflux as the valve is closed and pressure downstream from the valve is generally greater than pressure at a discharge orifice. Also, it is recommended that the rear plunger which displaces the valve stem be designed to be unresilient and have distally disposed geometry to provide a hard stop against the proximal end of the plunger valve stem to inhibit reflux resulting from flow stoppage by collision between the plunger valve stem and rear plunger rod.

Another approach involves using an inflexible interface between a shoulder on a plunger rod stem and a proximal edge of the associated syringe. As deliverable liquid volume is predetermined in the dual-chamber syringe of this example of a dual-chamber syringe, a hard stop provided by the shoulder on the plunger rod colliding with the proximal end of the dual-chamber syringe barrel is effective in inhibiting plunger motion which would cause reflux. Interestingly, presence of gas in the proximal chamber is still pressurized when a hard stop, following pressurized dispensing by force against the plunger rod is terminated by the collision. Relief of the pressure of the gas provides a continued gradual downstream liquid flow rather than reflux.

Measurement Indicia

In a dual-chamber syringe, indicia is needed for volumetric metering of contents of both the distal and proximal chambers. In a conventional single chamber syringe indica lines generally represent measurements of volumes to a fluid dispensing end. Length of indicia lines is commonly varied to provide visual discernment of major volume divisions. Four modes of volumetric measurement are provided. Note that, it should be the intent of design of devices made according to this invention to follow ISO guidelines for indicia, although there is no clear ISO specification related to dual-chamber syringes for proximal chamber and distal chamber content disclosure.

A first mode provides separate sets of indicia for metering each chamber (i.e. distal and proximal) and depends upon using each of the two plungers for measurement. One set provides a measurement which is limited on the proximal end by the maximum dose or distal chamber volume. As an example, in a 35 ml syringe, 20 ml may be allocated to dose volume (distal chamber) and 10 ml dedicated to a flush volume (proximal chamber). The 5 ml disparity between the sum of volume in the two chambers and syringe design volume provides space for the valve plunger and safety capacity for trapped and retained gas.

A second set of indica also utilizes both plungers for measuring and provides a measurement delineating from a point at which the reflux stop ends distal progress of the rear plunger proximal to an indication of maximum volume of the proximal chamber. Other indicia can provide such information as total provided volume and identification of type and concentration of liquid in the proximal chamber.

A second mode provides a common set of indicia lines for both chambers, providing a more customary representation of lines for a user, with volumetric numbering disposed on one side for the distal chamber and on the other side for proximal chamber. Similar allocations for distal and proximal chambers and allowance for valve and safety gas retention volumes as disclosed for the first set of indicia.

A third mode provides indicia disposed upon a plunger rod which is displaced to serially displace both plungers in a dual-chamber syringe. Only one contiguous column of indicia is required, with indicia provided in reverse order to that of a conventional syringe. Indicia indicating each respective unit of volume is numerically reduced proximally, thus indicating amount of fluid volume left in a referenced chamber. A reference line of measurement is between a proximal surface of syringe flanges and the respective surface marking on the plunger rod. For such a mode to be safe and effective, a known and fixed relationship must exist within required measurement accuracy of the syringe between the location of the plunger indicia and length of the proximal chamber and enclosing elements. Advantage of this mode is that only a single column of indicia is required, although the requirement for a proximal chamber to be of fixed, known and predetermined length and expansion and contraction of a gas bubble inside the proximal chamber affecting chamber length must be considered.

A fourth mode also provides a single column of indicia, but in this mode the indicia are disposed on the surface of the barrel as in the case of a conventional syringe. Also, as in the case of the conventional syringe, measurement is by viewing a distal edge of the plunger associated with the plunger rod only. Of course, indicia, while in a single column and being continuous, must be displaced to account for volume of a plunger valve. The same conditions as required for the third mode also apply to this mode. For such a mode to be safe and effective, a known and fixed relationship must exist within required measurement accuracy of the syringe between the location of the barrel indicia and length of the proximal chamber and enclosing elements. Advantage of this mode is that only a single column of indicia is required and measurement is made in the same way as for a single chamber syringe, although the requirement for a proximal chamber to be of fixed, known and predetermined length and expansion and contraction of a gas bubble inside the proximal chamber affecting chamber length must be considered and assured to permit measurement within specified accuracy.

Quality and Safety Assurance

Other than the prescribed safety practice for syringes, a dual-chamber syringe has but one additional quality assurance consideration needed. It is critical that no more gas than can be trapped and retained in the proximal chamber be therein. For a dual-chamber syringe valve which provides a closed conduit to a liquid only zone for liquid gas separation, a sure method for testing against too great a gas volume is performed with the simple steps of rotating the dual-chamber syringe such that the valve plunger is vertically disposed above the proximal chamber. When so disposed, gas must rise above the thus positioned bottom of the conduit. Both from a quality assurance standpoint and from a user test, safety of gas delivery prevention is assured when a line between the liquid and gas states is so disposed.

Sterilization Mode Compatibility

In past pre-filled syringe manufacture, it was common practice to fill syringes using sterile fill techniques. Recent FDA guidelines instruct use of gamma sterilization. To meet this requirement, only gamma stable synthetic resinous material comprising gamma stable polypropylene and butyl rubbers should be used for valve plungers, valve stems, barrels and plunger rod parts.

Complimentary Vessels and Interconnections

From a systems point of view, novel methods and combinations provide significantly improved products and techniques. While a dual-chamber syringe provides both opportunity to transport and deliver medicines in one chamber and a flush in a second chamber, long term storage of the wide variety of drugs likely requires extensive testing. Conversely, short term mixing and delivery of a wide variety of medicines in conventional single chamber syringes is commonly contemporarily practiced. The major advantage of a dual-chamber syringe over a single chamber syringe is commonly assessed as reduced requirements for interconnecting steps with associated user time and likelihood of contamination being prominent considerations. From this point of view, a source vessel, which provides liquid from a pre-filled syringe, having a complimentary fitting, such as a female luer fitting also significantly reduces assembly steps and, therefore, likelihood of contamination. For this reason, a novel provision for a female liquid source vessel provides a significant improvement in dual-chamber syringe safety and efficacy.

Closed Syringe Transfer System

Advantages of providing closed system transfer in a syringe is well known in hazardous drug handling art. Providing a syringe having a barrel which interfaces with a male adapter providing a valve which is only open when disposed within a female luer fitting provides a novel approach to constructing a dual-chamber syringe for closed system use. This novel invention comprises a tapered fitting valve integrally affixed to a syringe having a skeletal interface for the valve molded as part of the syringe barrel thereby replacing a conventional a male luer fitting of a syringe. Also a novel separate component which comprises the same novel valve construction as the syringe connected valve is disclosed.

Inventive Dual-Chamber Systems Object Summary

Accordingly, it is a primary object to provide novel dual-chamber syringe systems which incorporate one or more of the following novel objects:

It is a basic object to provide a dual-chamber syringe system comprising a plunger valve which does not cant and thereby distort barrel to plunger based indicia interpretation or result in liquid flow within valve to barrel ring interface.

It is a very important object to provide readily seen tamper evident indicators which provide assurance of dual-chamber system integrity.

It is an elemental object to provide a dual-chamber syringe system which provides visual evidence that an associated plunger valve is in a closed state before actuation procedure and in an open state following actuation.

It is a fundamental object to provide a dual-chamber syringe system which comprises structure and parts which operate to inhibit reflux upon completing delivery from the proximal chamber.

It is an important object to provide for presentation of measurement indica for dual-chamber syringe operation which provides for systematic differentiation between chamber content and dispensing measurement and which provides indicators which are consistent with ISO standards.

It is a critical object to provide quality assurance indicators used to assure that gas resident in a proximal chamber of a dual-chamber syringe is not greater than that which can be contained without delivery of gas from the syringe upon completing delivery from the proximal chamber.

It is a consequential object to provide a dual-chamber syringe universally comprising parts which are compatible with gamma sterilization.

It is an object to provide source liquid containers for use with a dual-chamber syringe system which reduce steps and time required for fluid transfer.

It is a meaningful object to provide a syringe which comprises a skeletal support for a tapered fitting valve which replaces the male luer fitting conventionally placed on a syringe such that the support and valve provide a male luer fitting which only open when disposed in a female luer fitting.

It is another meaningful object to provide a male luer adapter as a separate component which employs structure of the tapered fitting valve.

These and other objects and features of the present invention will be apparent from the detailed description taken with reference to accompanying drawings.

BRIEF DESCRIPTION OF THE DRAWINGS

FIG. 3 is a perspective of a valve plunger when disposed in a dual-chamber syringe.

FIG. 3A is a perspective of a valve plunger, similar to the valve plunger seen in FIG. 3, but comprising a different hollow interior.

FIG. 12 is a side elevation of a syringe barrel for a dual-chamber syringe showing a pattern of indicia disposed on the outer surface of the barrel.

FIG. 13 is a side elevation of a syringe barrel, similar to the barrel of FIG. 12, but comprising an alternate indicia pattern.

FIG. 17 is a cross section of the valve seen in FIG. 15 rotated to show disposition of an offset valve slit and a cavity disposed in a proximal portion of the valve.

FIG. 17A is a cross section of the proximal end of the valve.

FIG. 24 is a cross section of the valve seen in FIG. 17, rotated 90 degrees with a section taken in the plane of the slit and a skeletal support, seen in FIG. 26 disposed to provide a brace for the valve.

FIG. 25 is a cross section of a skeletal support for the valve seen in FIG. 17.

FIG. 26 is a cross section of the skeletal support seen in FIG. 17, but rotated 90 degrees.

FIG. 27 is a frontal elevation of the skeletal support seen in FIG. 25.

FIG. 36 is a perspective of a combination of a dual-chamber syringe and a female fitting syringe.

DETAILED DESCRIPTION OF THE ILLUSTRATED EMBODIMENTS

While the instant inventions disclosed herein are applicable to a wide variety of dual-chamber syringe applications and a number of tapered male/female insertion type fluid connectors, the detailed description provided herein is focused upon examples of medical devices. In this description, the term proximal is used to indicate that segment of a device which is a closest part to an object of reference. The term distal refers to an opposite orientation. Reference is now made to the embodiments illustrated in FIGS. 1-36 wherein like numerals are used to designate like parts throughout and primes of numbers generally indicate parts which are similar in shape and/or function of those numbers, but not exactly the same.

An Exemplary System

Figure 1:
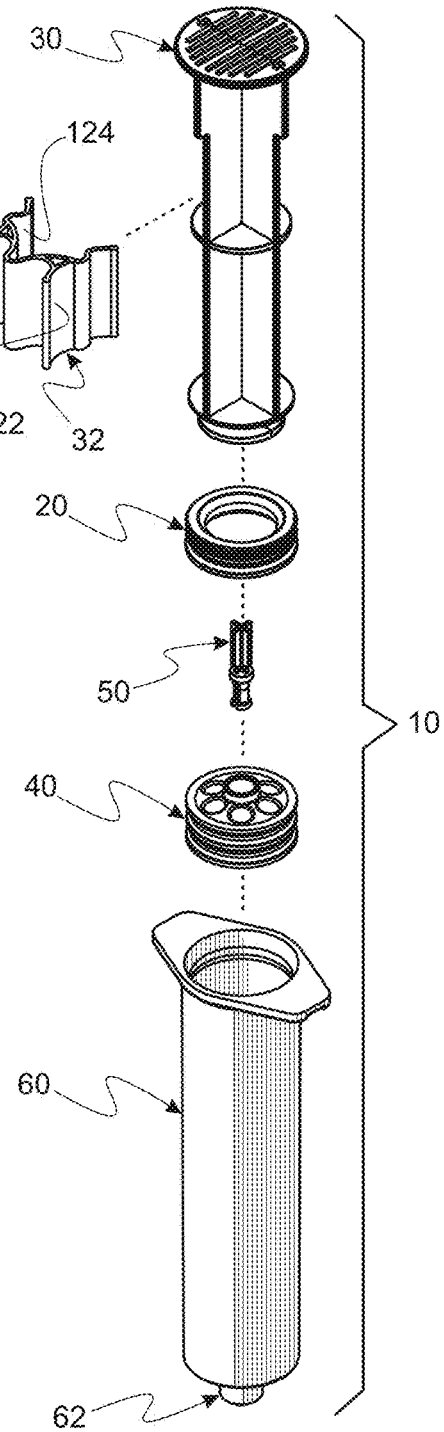
FIG. 1 is an exploded perspective of a presently preferred embodiment of a dual-chamber syringe made according to the instant invention.

Seen in FIG. 1 is an exploded view of parts which can be used to assemble a version of a dual-chamber syringe system 10, the parts being part of a system used to prepare and deliver medical preparations followed by a flushing liquid in a medical environment. While similar to art cited in the Continuity section provided supra, all but one of the parts, a plunger rod tip 20, has added novelty required for system's applications for dual-chamber syringes.

In addition to plunger rod tip 20, dual-chamber syringe system 10 comprises a rear plunger rod 30 used to directly displace tip 20 and an associated plunger rod sleeve 32, a plunger 40 which is part of a normally closed valve, an actuating stem 50 which is disposed within a valved pathway of plunger 40 to form a plunger valve 70 and displaced to open a fluid pathway within plunger 40 thereby providing a normally closed valve, and a conventional syringe barrel 60. Barrel 60 comprises a male luer lock fitting 62 for drawing and dispensing fluid. Application and need for sleeve 32 is fully disclosed hereafter.

A Pre-Filled System

Figure 8:
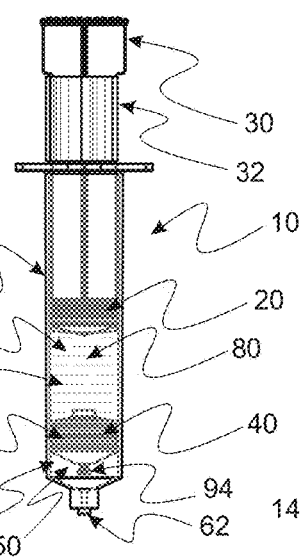
FIG. 8 is a cross section of the dual-chamber syringe seen in FIG. 7 syringe inverted to continue dispensing liquid from the distal chamber.

An assembled dual-chamber syringe system 10 is seen in FIG. 8. Actuating stem 50 is displaced into plunger 40 to form plunger valve 70. A chamber 80 disposed between plunger valve (valve) 70 and plunger rod tip 20 contains a fluid 84 and is anticipated to comprise both a liquid 84 and a gas 86. It is preferred that chamber 80 be pre-filled by a manufacturer before delivery to a site of use. As is well known in medical syringe use art, unless otherwise prescribed, only liquid should be dispensed from chamber 80 with all gas remaining resident in chamber 80 at the end of a chamber 80 dispensing cycle.

A second chamber 90, disposed between valve 70 and fitting 62, is kept disparate from chamber 80 for sequential fluid delivery by action of valve 70 as disclosed in detail hereafter. Fluid withdrawal and dispensing associated with chamber 80 is conducted by displacing plunger rod 30 in the same manner as fluid is manipulated in a conventional syringe and is performed prior to dispensing liquid from chamber 80.

Displaceable Stem Plunger Valve

Figure 2:
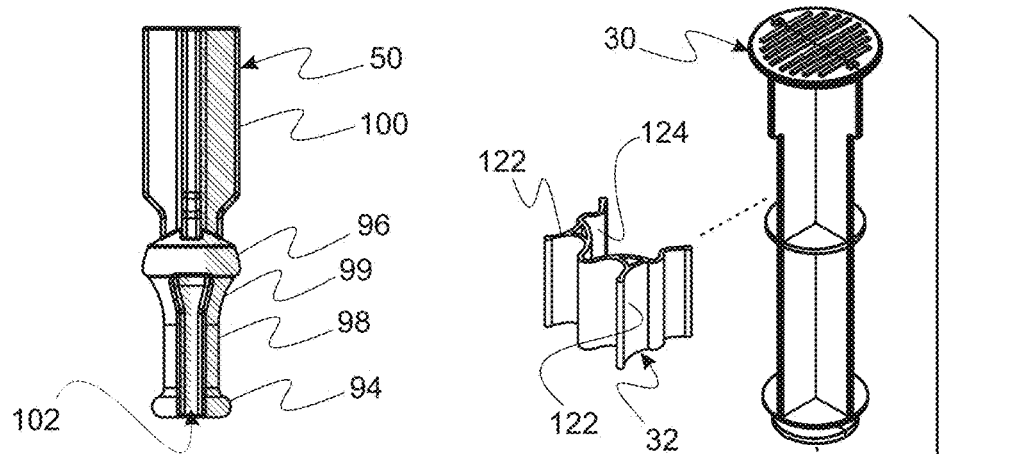
FIG. 2 is a magnified side elevation of a valve stem made according to the instant invention.

A magnified view of stem 50 is seen in FIG. 2. Generally, stem 50 comprises an enlarged footing 94 sized to collide with syringe barrel 50 at a distal dispensing hole without inhibiting flow through the hole and a bulbous central portion 96 which is sized to obstruct the fluid pathway of plunger 40 when disposed therein. Between footing 94 and portion 96, stem 50 comprises a substantially constant diameter, linear extension 98 which leads to a conical segment 99. Bulbous portion 96 is shaped to be retained by compression within the valve plunger 40 pathway until stem displacement and compressive forces act to extricate stem 50 from the pathway. Once that condition occurs, the shape of conical segment 99 is acted upon by the interactive compressive forces associated with barrel 60 and plunger 40 to further expel bulbous portion 96 from the pathway. A channel 102 which is disposed along footing 94, extension 98 and segment 99 provides an open passageway for fluid flow when bulbous portion 96 is outside the pathway.

Stem 50 further comprises a finned section 100 having a plurality of bladed parts which provide for stability within the pathway and a clear fluid path. Length of section 100 is an important dimension as disclosed in detail hereafter.

A magnified image of a proximal side of plunger 40 is seen in FIG. 3. Similar plungers are disclosed in art from which U.S. patent application continues-in-part. However, plunger 40 does not require a separate support ring disposed to provide a brace against canting and other unwanted off-axis displacement, as formerly disclosed in previous art cited supra.

Rather, plunger 40 comprises integral support structure which provides open space for gas capture and yet added rigid support provided for communicating plunger rings against an associated internal syringe barrel wall. Those familiar with syringe fabrication art well understand effect of non-homogeneous surface friction distribution, knowing that a variance in such distribution, if not accounted and corrected for, can cause a plunger, which is displaced only by fluid communication, to cant (be angularly displaced relative to a long axis of a syringe barrel). Such canting can result in either unwanted communication between fluids in otherwise disparate chambers or misreading volumetric measurements made between indicia on barrel 60 and a predetermined measurement edge-site on plunger 40.

Canting Protection

To guard against such canting, plunger 40 comprises a plurality of air-capturing holes, commonly numbered 110 which are closed on a distal side (not shown), surrounded by a support structure 112 constructed to maintain a firm and compressive contact against an associated barrel 60 internal surface. Structure 112 also provides a make-up which maintains integrity of a tube 114 which surrounds and provides an entrance to fluid pathway 116 from a liquid only zone disposed within a fluid fulled chamber of barrel 60. While many different geometries can provide such support, structure which comprises the support structure about hollow cylinders is preferred.

An alternate plunger 40' is seen in FIG. 3A. While it is effective to reduce canting to an acceptable level using support structure 112 (seen in FIG. 3, holes 110 associated with such structure can harbor gas during a filling process. Such a gas refuge can be eliminated with a larger cone-shaped cavity 110'. However, cavity 110' yields a thinned wall 111 near a proximal ring 111'. As rings, such as ring 111', are generally oversized relative to an internal surface of a barrel, such as barrel 60 (see FIG. 1), to assure sufficient compression to be fluid tight against the barrel, a variation in size of plunger rings can also be used to reduce canting. As an example, a distal ring 111" of plunger 40' can be oversized by four percent while ring 111' can be oversized by 6 six percent. Such variation in oversizing produces a compressive force in the region of ring 111' which compensates for thinning More details concerning delivery of only liquid from the liquid only zone is provided hereafter.

Figure 4:
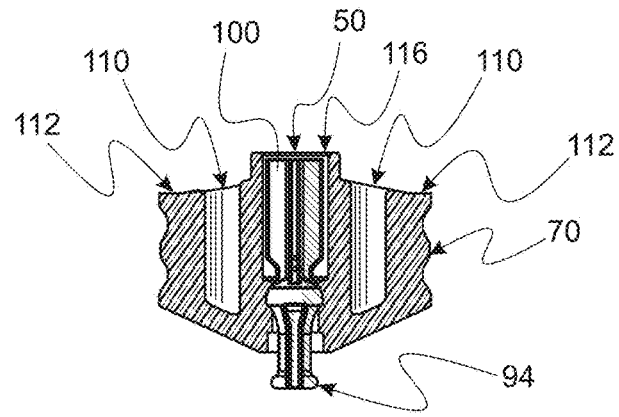
FIG. 4 is a perspective of a valve stem disposed in a valve plunger such that a pathway in which the stem is disposed is closed to fluid flow.
Figure 5:
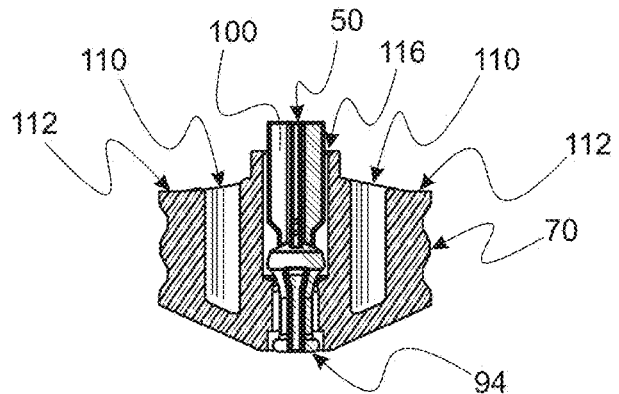
FIG. 5 is a perspective to the valve stem and plunger seen in FIG. 2 with the valve stem displaced to open the pathway to fluid flow.

Valve State, Tamper Evidence Indicators and Premature Valve Actuation Protection Reference is now made to FIGS. 4 and 5 wherein a stem 50 is disposed to close pathway 116 in FIG. 4 to form a closed state of a plunger valve 70. Note that plunger valve 70 is in an open state in FIG. 5 resulting from displacement of stem 50. Further note that, when plunger valve 70 is in a closed state (FIG. 4), footing 94 is visible outside plunger 40 and section 100 is not seen. When plunger valve 70 is in an open state, stem 50 has sufficient length that section 100 is visible outside plunger 40 and footing 94 is hidden.

Knowledge of the state of plunger valve 70 is critical in determining validity of usefulness of dual-chamber syringe system 10. Display of footing 94, as seen in FIGS. 6-9 provides assuring evidence that no tampering or inadvertent valve actuation has occurred. For when footing 94 is so visible, plunger valve 70 is closed. Such is the case in FIGS. 6-9.

Figure 7:
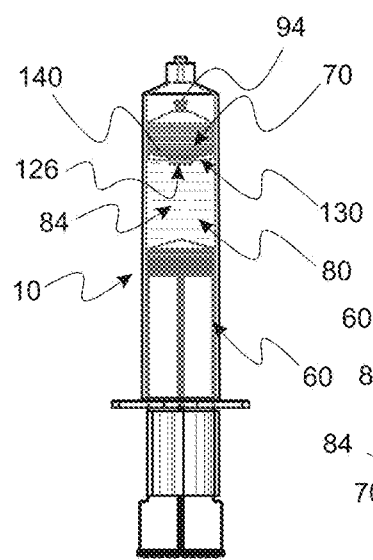
FIG. 7 is a cross section of a dual-chamber syringe similar to the syringe seen in FIG. 6 but rotated to provide a measurement of gas residing in the proximal chamber.

To guard against premature opening of plunger valve 70, a removable sleeve 32, seen in FIGS. 7 and 8, provides a guard when affixed to plunger rod 30. So affixed, a barrier is provided to prevent footing 94 being displaced into contact with barrel inner surface wall 120 resulting in such valve opening. With sleeve 32 in place, plunger rod 30 can be displaced arbitrarily without inadvertent plunger valve 70 displacement to a valve 70 open state. As is seen in FIG. 1, sleeve 32 comprises opposing wings, commonly numbered 122, which are "pinched" to spread attaching legs, commonly numbered 124, for removal from rod 30. Once sleeve 32 is removed reference for dual-chamber syringe 10 is changed herein to dual-chamber syringe 10'. Sleeve 32 can be made by extruding polypropylene.

Figure 9:
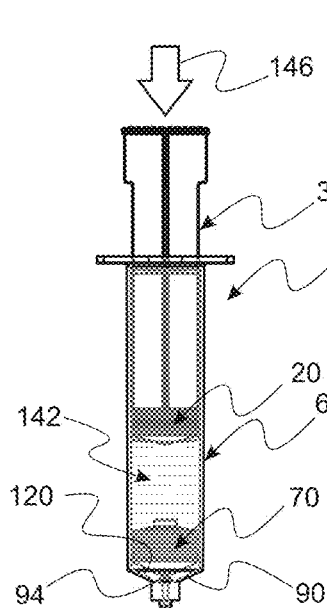
FIG. 9 is a cross section of the dual-chamber syringe seen in FIG. 8 with a distal portion of a stem impacting an inner surface of the barrel of the associated syringe.
Figure 10:
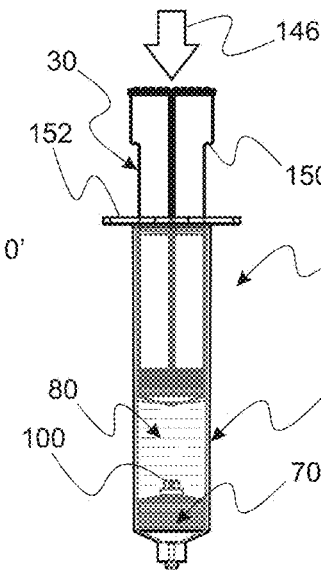
FIG. 10 is a cross section of the dual-chamber syringe seen in FIG. 9 with the stem displaced such that the proximal portion of the stem is visible, such viability indicating actuation of the valve plunger to an open state.

Other than delinquent tampering, a plunger valve 70 of a dual-chamber syringe system 10' could be inadvertently and improperly triggered to an open state simply by premature displacement of stem 50 against in internal surface wall 120 of barrel 60 after safety sleeve 32 is removed. Displacement for triggering plunger valve 70 is seen in FIGS. 9 and 10. Note that sleeve 32 is no longer affixed to plunger stem 30. Note that such displacement is made evident by disappearance of footing 94, which is seen in FIG. 9, but unseen in FIG. 10. Also, section 100, being clearly visible as in FIG. 10, indicates transition of plunger valve 70 to an open state and is not seen in FIG. 9. Of course, operation of dual-chamber syringe system 10' after premature opening of plunger valve 70 should be avoided and evidence of such is critical.

Proximal Chamber Considerations and Obviation of Gas Delivery

For many purposes a dual-chamber syringe system 10 is delivered from a manufacturer proximal chamber 80 being pre-filled (see FIG. 8). Different from distal chamber 90 of system 10, gas is not easily purged from chamber 80 immediately prior to use. As seen in FIG. 3, valve plunger 40 comprises tube 114 which has an entry orifice 126 set apart a predetermined distance from holes 110. Space within holes 110 and from holes 110 to just short of orifice 126 is provided for accumulating gas which is kept away from orifice 126 by physical material state properties thereby forming a liquid only zone. It is preferred that holes 110 be asymmetrical such that gas is not retained in the holes 110 when vertically oriented with hole 110 orifices open upwards. It should be recognized that only a limited volume of gas can be so retained. For this reason, a quality assurance procedure provides opportunity to confirm gas-free delivery and safety of system 10'. As seen in FIG. 7, to perform quality control procedures during manufacturing and before use, a dual-chamber syringe system 10 (or 10') is held upright and the relative level of a liquid/gas interface is determined to be above orifice 126. As seen in FIG. 7, for safety, the gas/liquid interface 140 resides above orifice 126 when system 10 (or 10') is so oriented. It should be noted that holes are but one alternative for providing space for collection of gas. As an example, a shallow cavity which permits the same space as the volume of gas which can be resident in holes 110 can be used within the scope of the invention.

Further, it should be noted that gas within the pathway associated with orifice 126 should be cleared of gas by the filler (e.g. manufacturer) at the time of filling. Due to the liquid only zone, no further consideration need be given to gas resident in the pathway. However, when filling chamber 90, care should be taken to purge gas from all parts of chamber 90 including the distal portion of the pathway associated with orifice 126. Such care is generally performed for purging gas from filled conventional syringes before dispensing.

Filling and Dispensing the Dual-Chamber Syringe

Figure 6:
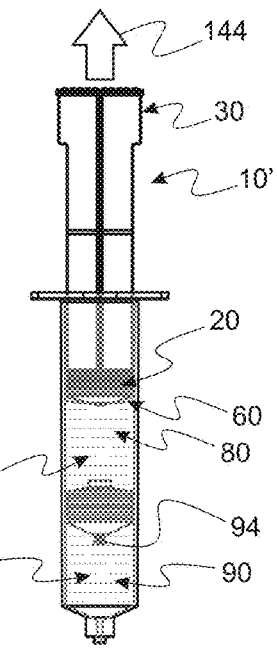
FIG. 6 is a cross section of an assembled dual-chamber syringe wherein a plunger valve divides a syringe barrel into two disparate chambers, both chambers being filled with liquid.

Sleeve 32 should be retained in place while chamber 90 is being filled. Generally, a fluid 142 is drawn into barrel 60 by displacing plunger rod 30 in direction of arrow 144. Once a fluid 94 is resident in chamber 90, sleeve 32 can be removed, as seen in FIG. 6. Dispensing of fluid 94 from chamber 90 is accomplished by displacing plunger rod 30 in direction of arrow 146. As seen in FIG. 9, near the end of chamber 90 dispensing cycle, footing 94 collides with syringe inner surface 120. As footing 94 is further displaced, chamber 90 is fully emptied. As seen in FIG. 10, at the end of a chamber 90 dispensing cycle, footing 94 is no longer visible and section 100 provides an indicator for a plunger valve open state, ready for flushing delivery from chamber 80.

Guard Against Refluxive Flow at the End of a Flushing Cycle

Figure 11:
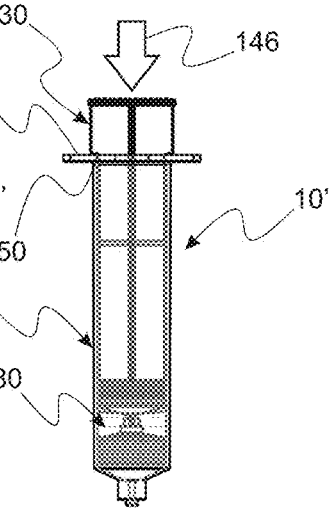
FIG. 11 is a cross section of the dual-chamber syringe seen in FIG. 10 at the end of a proximal chamber dispensing cycle with further displacement of a plunger rod being impeded by collision of shoulders of the plunger rod with proximal portions of the syringe barrel.

Continued displacement of plunger rod 30 in direction of arrow 146, as seen in FIG. 11, dispenses flushing liquid. It is important to consider the state of system 10' at the end of the flushing cycle. First, it is important to note that the flushing cycle should be terminated before any gas has been dispensed from chamber 80. Of equal concern is that, at the end of a chamber 80 dispensing cycle, any refluxive flow back into system 10' is undesirable. It is common knowledge to those skilled in patient care that such flow can produce an unsafe condition for an interconnected patient (e.g. through a catheter). In system 10', there are two methods for obviating refluxive flow. A first method involves reintroducing bulbous portion 96 into a sealing state within pathway 116. (see FIGS. 4 and 5) by displacing plunger tip 20 against section 100 of stem 50 However, length of stem 50 may not effect reintroduction of portion 96 sufficiently to close plunger valve 70.

A second and preferred method is by providing a "hard" stop against continued displacement of plunger rod 30 and associated tip 20. It may be noted that gas within chamber 80 at the end of a flushing cycle has a sufficiently high pressure to assure continued dispensing at a moment when displacement of plunger 30 ends. However, if there is any concurrent reflexive action, such as may occur due to resiliency of tip 20 against stem 50 at section 100, dynamics of such reflexive action are generally slower than pressure reduction in gas in chamber 80. As such reflexive action is counter to direction of plunger rod 30 displacement and slower than chamber 80 pressure reduction, the result being a material volumetric displacement which produces refluxive flow.

For this reason, system 10' preferably employs a hard stop. Such a hard stop is provided in system 10' by a collision between a shoulder 150 strategically disposed as an outwardly extending part 151 of plunger rod 30 and a flanged proximal portion 152 of barrel 60, as seen in FIG. 11. Such a hard stop, without reflexive motion has proved to take advantage of pressure resident in gas in chamber 80 to produce a limited amount of dispensing flow at the end of a flushing cycle which would not otherwise occur should there be a reflexive response.

Indicia Alternatives

Volumetric measurement of fluid dispensed from a dual-chamber syringe, such as syringe 10', produces needs for indicia presentation previously not required for single chamber syringes. As may be noted in FIGS. 6 and 9, regions along barrel 60 (of syringe 10') have different starting points and delivery sectors for fluid dispensed from each chamber 80 and 90. For purposes of this discussion, distal chamber 90 shall be considered to be a drug delivery chamber and proximal chamber 80 shall be considered to be a flush delivery chamber. One exemplary pattern of indicia is provided in each FIG. 12 and FIG. 13. A first item to note is that all of the effective measurement indica, generally numbered 200 in FIG. 13, are disposed at a distal end of barrel 60. Referring to FIG. 12, it may be noted that separate measurement lines, identified as 210 and 220, are provided for contents of each chamber 80 (dose fluid) and chamber 90 (flush), respectively. Of necessity, due to sequential delivery of system 10' contents and space required for plunger valve 70 and a gas safety reservoir, indicia scales ( 210 and 220 ) and related numbers are offset and overlapping.

Similarly, there is an overlapping pattern seen in FIG. 13. However, common indicia lines 230 are provided for both drug and flush metering. A separate set of numerical measurement indicators (240 and 250) is provided for differentiating metering of dose and flush, respectively.

An advantage of indicia layout in FIG. 12 is that the two sets of indicia for dose and flush are entirely separate. As such, flush indicia 220 are not required to have a line-to-line correspondence and better use of available barrel 60 space than for the pattern of indicia in FIG. 13, results. A marked advantage of indicia layout in FIG. 13 is the provision for use of common indicia lines. Another consideration one must take into consideration is a likelihood of confusion about indicia used for measurement of drug or flush (i.e. that which is effective during each system 10' dispensing cycle). For this purpose, it is recommended that color differentiation be provided to differentiate dispensing of contents from chambers 80 and 90, as seen in FIG. 12.

Still another consideration for indicia patterns, seen in FIGS. 12 and 13, is that line indicia are not required along the length of barrel 60 as is commonly the case in conventional syringes. Generally the most proximal line along a conventional barrel is also an indicator for limiting proximal displacement of a plunger rod and associated tip. For this purpose, a limit line 260 is provided as seen in each FIGS. 12 and 13. It should be noted that a basic advantage for patterns seen in FIGS. 12 and 13 is that measurement of volumes in each chamber is independent of fluid quantities in the other chamber. However, use of these patterns does require a change of plunger reference when switching from dispensing from one chamber to another.

It is well known that conventional single chamber syringes have a dead space (volume of undeliverable fluid) disposed in the space between the barrel and distal end of the male luer fitting. As such does not exist in a distal chamber of a dual-chamber syringe (due to distal chamber flushing following dispensing from the distal chamber), a correcting offset in an associated indicia pattern is required for delivery of otherwise undispensed fluid.

Figures 13A, 13B, 13C, 13D, 13E:
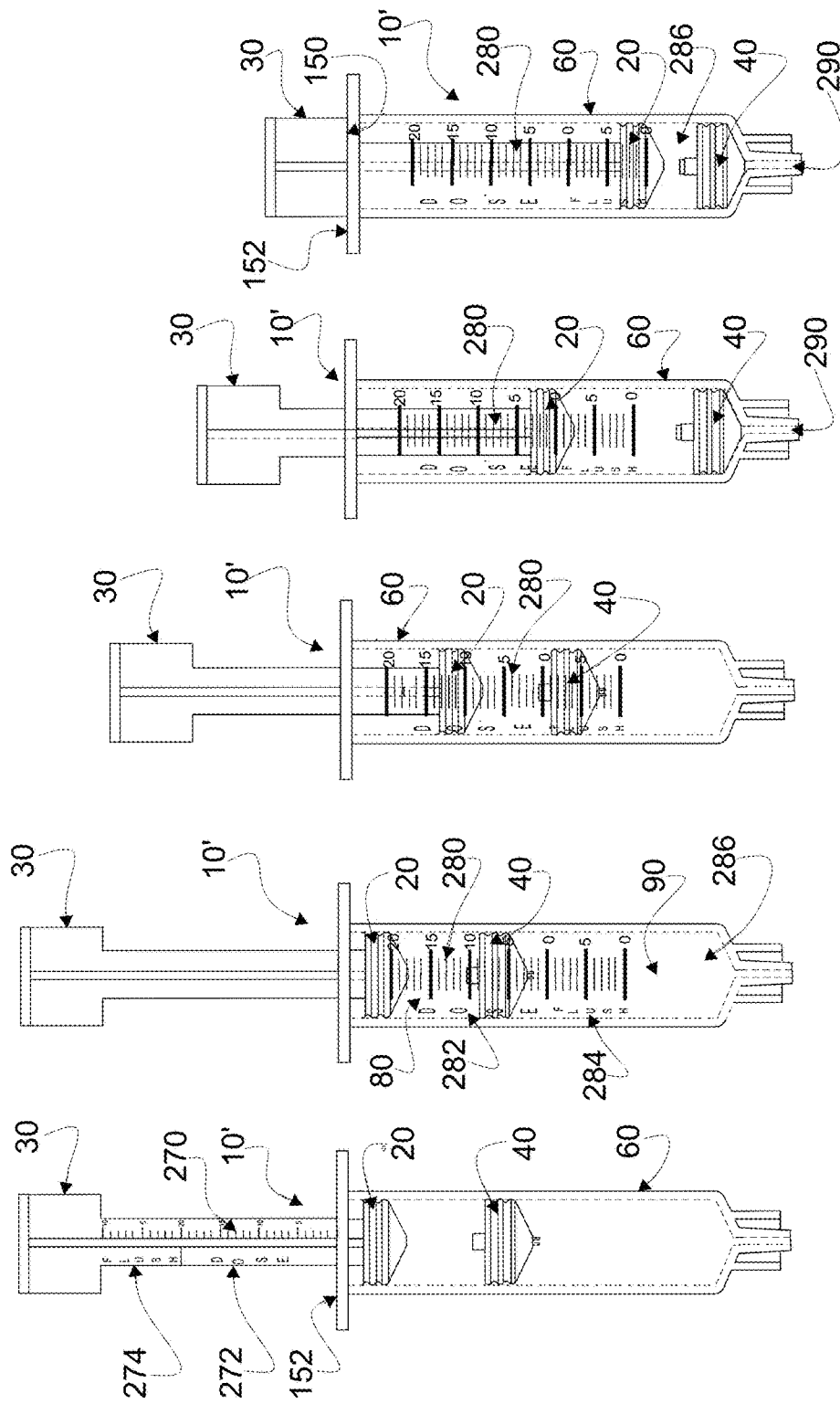
FIG. 13A is a side elevation of a syringe barrel and associated plunger rod and plunger tip comprising indicia disposed on the plunger rod.
FIG. 13B is a side elevation of a syringe barrel and plunger rod, similar to FIG. 13A, but with a pattern of indicia proximally disposed on the syringe barrel.
FIG. 13C is a side elevation of a syringe barrel and plunger rod showing an indicia pattern which is similar to the pattern of FIG. 13B, but specifically designed for flush and dose volumes different than those seen in FIG. 13B.
FIG. 13D is a side elevation of the syringe barrel and plunger rod seen in FIG. 13C with a plunger valve and associated plunger rod tip displaced to empty a distal chamber.
FIG. 13E is a side elevation of the syringe barrel and plunger rod seen in FIG. 13D with the plunger valve and plunger rod tip displaced to complete dispensing from a proximal chamber of the dual-chamber syringe.

If it is preferred to measure all dispensed volumes by reference to a single plunger (such as plunger tip 20 (see FIG. 1), indicia seen in FIGS. 13A-13E may be employed. In FIG. 13A, indicia pattern 270 comprises a single linear line of volumetric measurement marks and descriptors 272 and 274 for dose and flush, respectively. It is important to note that for a single linear line of volumetric measurement lines to be used, the linear distance between plunger tip 20 and plunger valve must be of known predetermined length and held constant in all such dual-chamber chamber syringes 10'. Such is true for all indicia seen in FIGS. 13B-13D, as well. In the case of measurement being made by displacement of plunger rod 30, measurement is made at the interface between syringe barrel flange 152 and a respective coinciding mark of indicia pattern 270 on stem of rod 30.

As seen in FIGS. 13B-13E, a set of indicia lines 280, comprise a single linear line of marks for both dose and flush. In this case, the distal edge of plunger tip 20 provides the measurement reference line (as is the case for single chamber syringes). Note that dose (282) and flush (284) patterns are reversed on indicia of FIG. 13B compared to indicia of FIG. 13A. Note also that there is a blank region 286 where no indicia is printed. Region 286 represents space for plunger volume and fluid (liquid and gas) residual in chamber 80. Since plunger tip 20 is restricted from further displacement by contact of shoulder 150 with flange 152 (see FIG. 13E) no volumetric measurement is required in region 286.

Dispensing steps are seen in sequence in FIGS. 13B to FIG. 13E. A syringe 10' comprises filled chambers 80 and 90 for a twenty ml dose in FIG. 13C and a 10 ml dose in FIG. 13C. No markings denoting fluid (gas or liquid) content in barrel 60 is provided to guard against confusion with indicia marks. In FIG. 13D, all dose, except that contained in dead space in the throat 290 of barrel 60, is dispensed. In FIG. 13E, liquid in chamber 80 is dispensed along with dose remaining in throat 290.

Figure 13F:
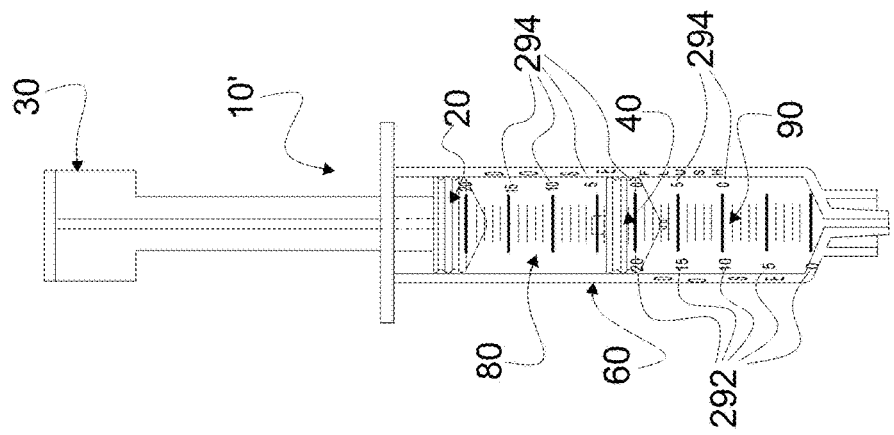
FIG. 13F is a side elevation of a dual-chamber syringe similar to the syringes seen in FIGS. 13A-E, but with another indicia pattern.

Still another indicia pattern is seen in FIG. 13F. As it may be preferable to fill and measure volumes in chamber 90 using the most distal plunger (plunger valve 40), a set of indicia numbers (generally referenced by 292) are provided as seen on the left side of barrel 60. Later, when dispensing a set of indicia numbers (generally referenced by 294) are provided as seen on the right side of barrel 60. It should be noted that use of indicia 292 provides a direct and accurate measure for volumetric measurement of fluid in chamber 90, while use of indicia 294 provides a measurement independent of canting of plunger valve 40.

As system 10 can be delivered as a dual-chamber syringe with one chamber pre-filled, it is recommended that all parts used in system 10 be compatible with gamma sterilization.

Tapered Valve Fittings for Closed System Operation

One of the major applications for dual-chamber syringe systems is in dispensing oncology drugs where need for a closed system is preeminent. Of course, oncology uses are not the only applications for dual-chamber syringe systems, but the toxic nature of oncology drugs has produced a significant impetus for the development of closed systems.

Figure 14:
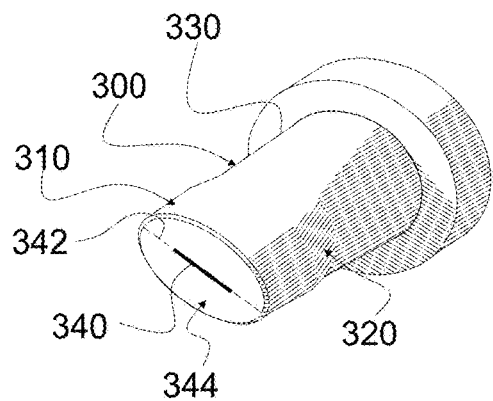
FIG. 14 is a perspective of a valve for a tapered fitting with a medically disposed slit.

Reference is now made to FIGS. 14-35 wherein a valve for tapered fittings is disclosed. As seen in FIG. 14, a valve 300, made according to the instant invention, is seen. Valve 300 comprises four separate sections, an elliptically shaped slit valve 310, a transition section 320 and a circularly shaped portion 330. For a valve 300 to be used with a female tapered luer fitting, each section comprises a 3° taper.

Similar to a back-to-back valve disclosed in Thorne 681, slit valve 300 comprises an internal cavity disposed to provide a closing force upon medially disposed slit 340 when acted upon by internal syringe pressure. The cavity portion of valve 300 is part of back-to-back valving which is only opened by compressing slit valve 300, preferably into a circular shape. Further, as in all the art from which this U.S. Patent Application continues, slit 340 is medially disposed, in this case along a major axis 342 of an elliptical face 344 of valve 300. Due to very limited space available within a luer fitting and a need for a cavity whereby fluid pressure within the valve compresses slit 340 to obviate syringe dispensing flow, a medially disposed slit 340, seen in FIG. 14, the space for both a cavity and adequate wall thickness in the region of the cavity is not adequate for a reasonable design.

Figure 15:
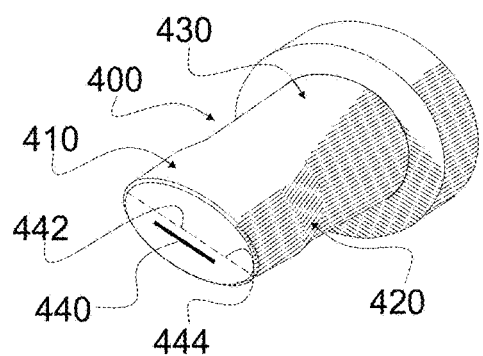
FIG. 15 is a perspective of a valve similar to the valve seen in FIG. 14, but with a slit offset from a medial line (major axis of an ellipse).

To accrue a better utilization of available space within dictates of luer fitting dimensions, a different slit valve 400, seen in FIG. 15, valve 400 comprises similar sections to valve 300 comprising an elliptically shaped slit valve actuator 410, a transition section 420 and a circularly shaped portion 430. However, in valve 400, a slit 440 is offset from a major elliptical axis 442, indicated by a dashed line 444. As is clarified hereafter, establishing slit dimensions, which determines a hole diameter which is formed by compressively deforming elliptical valve parts to circular parts which conform to a female luer fitting into which valve 400 is inserted, also can be used to determine major and minor axis dimensions of valve 400 with an offset slit, as disclosed hereafter.

Figure 16:
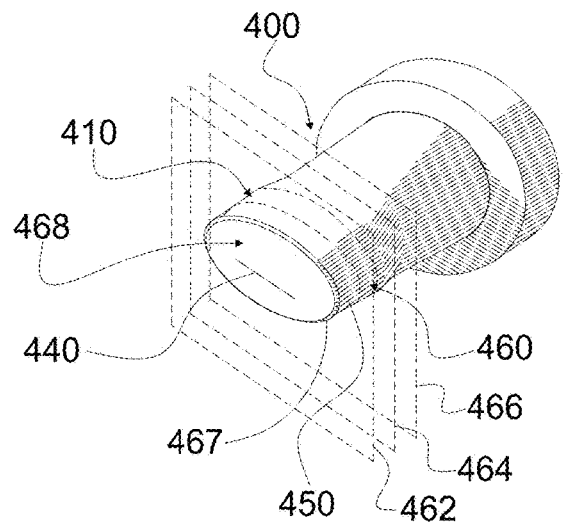
FIG. 16 is a perspective of the valve seen in FIG. 15 with three intersecting planes disposed at the distal face, medial section and proximal face of the valve, respectively.

Reference is now made to FIG. 16. Valve actuator 410 comprises a distal part 450 and proximal part 460. Extremities of parts 450 and 460 are distinguished by cross-cutting planes 462, 464 and 466. Plane 462 is disposed across a face 468. Plane 464 is disposed between parts 450 and 460. Plane 466 is disposed at the most proximal extremity of part 460. A slit 440 is disposed offset from a major axis (not shown) of an ellipse 469 at the plane 462 of face 468.

Valve 440 is seen in a side cross-cut view in FIG. 17. Part 450 is seen to be solid, except for slit 440. Part 460 comprises both a cavity 480 and slit 440. As mentioned supra, cavity 480 permits pressurized fluid to be applied orthogonal to the plane of slit 440 effecting closure when valve 440 is not compressively opened by insertion into a tapered fitting. A wide collar 481 is disposed on a proximal end of valve 440 for sealing installation as disclosed hereafter.

A cross section of part 460 in plane 466 (see dashed line 470 in FIG. 17) is seen in FIG. 17A. Disposition of slit 440 below cavity 480 (and an associated major elliptical axis permits a wider wall thickness, indicated by numbers 482 and 484 than possible if slit 440 is disposed on the major axis).

Referring once more to FIG. 17, a valve 400 comprises a hole 490 which is closed internally at plane 466 (see FIG. 16) which is the proximal end of valve actuator 410. As material from which valve 400 is made must be supple to be compressed to open slit 440 and must be rigid enough to be effectively fully inserted into a tapered female fitting, an inner skeletal support is needed. As seen in FIG. 25, such a skeletal support 500, preferably injection molded of syringe compatible polypropylene, is sized and shaped to fit snugly within hole 490. As better seen in FIG. 26, support 500 comprises distal extensions, generally numbered 502, at the end of a support member 504. A collar 506 is provided for assembly support. A thru hole 510 provides a fluid communication pathway. Distal extensions 502 provide skeletal support for inserting valve actuator 410 while also providing a space for a fluid pathway for an opened slit 440 to cavity 480. An end-on view of support 500 is seen in FIG. 27.

A cross section, in the plane of slit 440 is seen in FIG. 24 to comprise a skeletal support 500 and a valve 400 which combine to provide an insertable valve 600. Unless valve 400 can be made with sufficient rigidity to be self-supporting, skeletal support 500 should be provided. As disclosed hereafter, such support may be provided by an associated housing.

Figure 18:
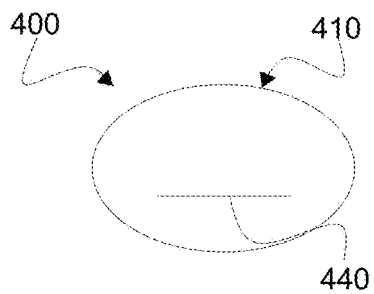
FIG. 18 is a cross section of the proximal face of the valve seen in FIG. 17.
Figure 21:
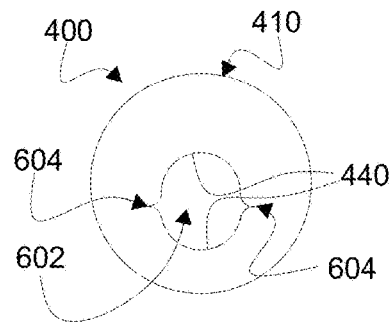
FIG. 21 is a cross section of the elliptically shaped valve seen in FIG. 18 compressed to a circular shape.
Figure 19:
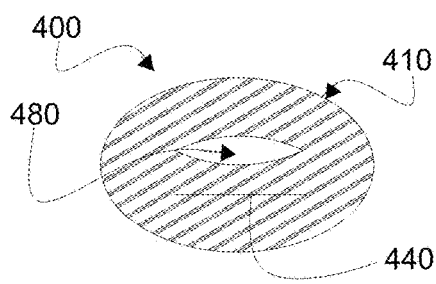
FIG. 19 is a cross section at a medial plane, seen in FIG. 16, of the valve seen in FIG. 17.
Figure 22:
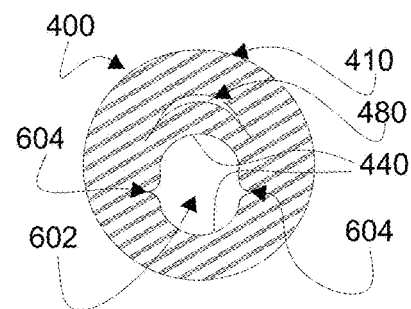
FIG. 22 is a cross section of the elliptically shaped valve seen in FIG. 19 compressed to a circular shape.
Figure 20:
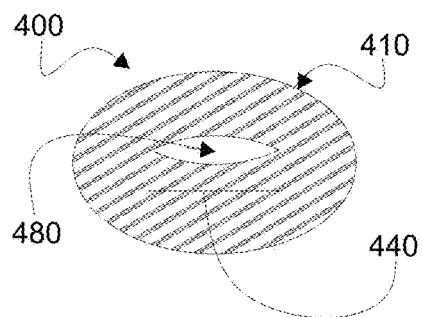
FIG. 20 is a cross section at a proximal plane, seen in FIG. 16, of the valve seen in FIG. 17.
Figure 23:
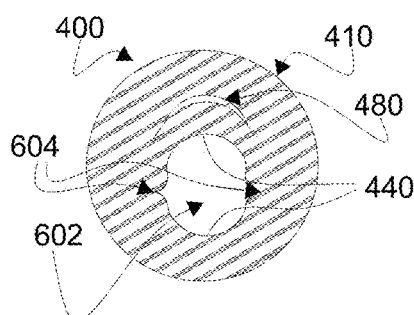
FIG. 23 is a cross section of the elliptically shaped valve seen in FIG. 20 compressed to a circular shape.

Reference is now made to FIGS. 18-23 which provide comparisons between closed and open slits. Seen in FIG. 18 is a closed slit disposed across plane 462; similarly, FIGS. 19 and 20 disclose closed slits associated with planes 464 and 466, respectively. FIGS. 21-23 are disposed in the same planes as FIGS. 18-20, respectively. Compressing valve actuator 410 within a circular tapered fitting results in valve 400 being opened as seen in FIGS. 21-23. Note that volume of cavity 480 is reduced while a through hole 602 is opened. Due to physical material constraints, hole 602 may not be round, but have acute lip separations at slit ends, generally numbered 604. For this reason, slit 440 should be lengthened beyond pi times desired hole diameter.

Figure 28:
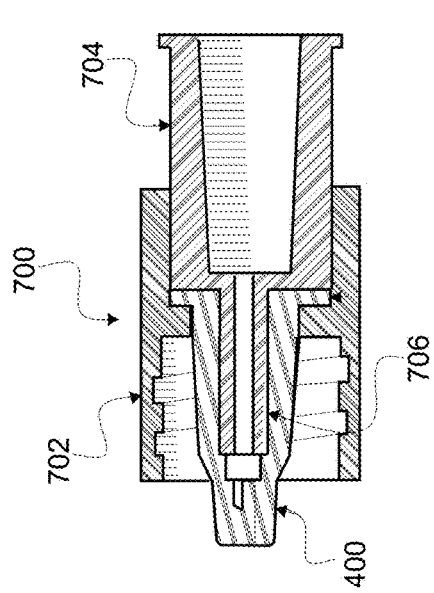
FIG. 28 is a cross section of a male adapter device comprising a valve for a female tapered luer fitting.
Figure 29:
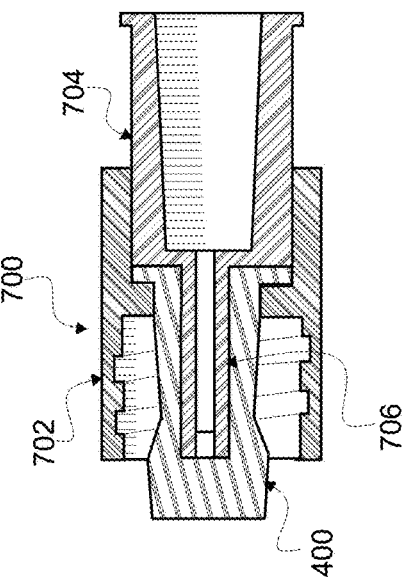
FIG. 29 is a cross section of the male adapter device seen in FIG. 28, rotated 90 degrees.

An insertable valve according to the instant invention may be assembled as a stand-alone male adapter 700 from three parts. As seen in FIGS. 28 and 29, male adapter 700 comprises a valve 400, a male luer lock fitting 702 and a female luer lock fitting 704. Female fitting 704 comprises an integrally molded skeletal support 706 (which is consistent in form and function with skeletal support 500 seen in FIGS. 24-26.

Figure 33:
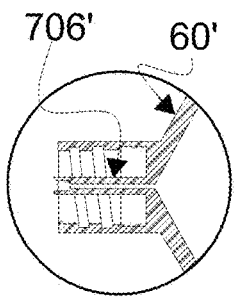
FIG. 33 is a magnified copy of the circled portion of the barrel seen in FIG. 30.
Figure 30:
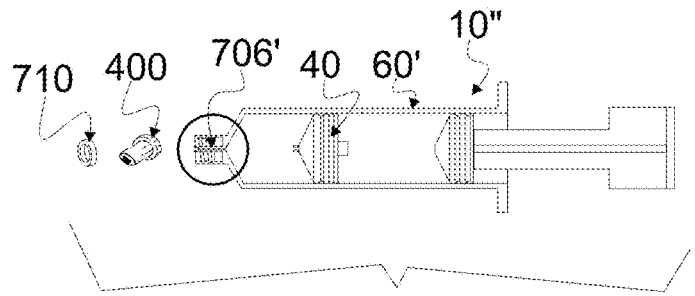
FIG. 30 is an exploded view of parts for a dual-chamber syringe having a barrel which is structured to employ a valve for a tapered luer fitting.
Figure 34:
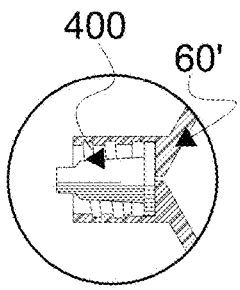
FIG. 34 is a magnified copy of the circled portion of the barrel seen in FIG. 31.
Figure 31:
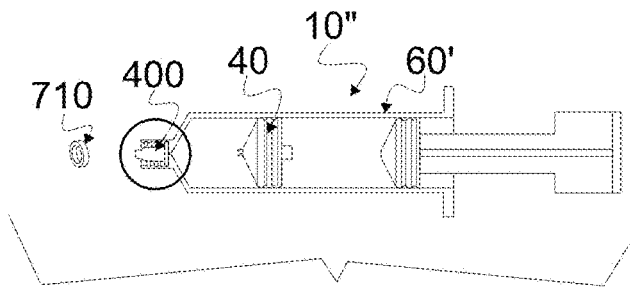
FIG. 31 is an exploded view of the parts seen in FIG. 30 with a valve affixed to provide a male luer fitting for the dual-chamber syringe.
Figure 35:
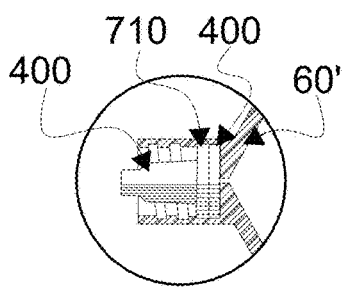
FIG. 35 is a magnified copy of the circled portion of the barrel seen in FIG. 32.
Figure 32:
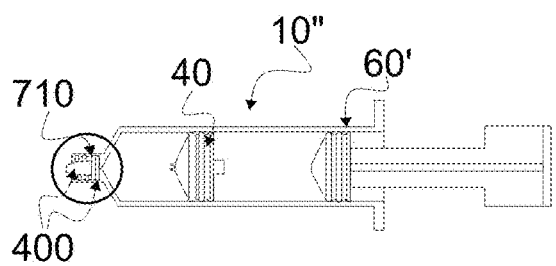
FIG. 32 is a cross section of a fully assembled dual-chamber syringe with barrel affixed with the valve and compression ring.

For syringe applications, a conventional syringe barrel, such as barrel 60 (see FIG. 1), can be modified to provide a skeletal support as seen in FIGS. 30 and 33. As best seen in FIG. 33, rather than a conventional male luer fitting, barrel 60' comprises a skeletal support 706' which, like support 706 (see FIGS. 28 and 29) is consistent in form and function with skeletal support 500 seen in FIGS. 24-26. Assembly of a dual-chamber syringe with an associated valve 400 is seen in FIGS. 30-32. A valve 400, seen separate in FIG. 30, is disposed about skeletal support 706' as seen in FIGS. 31 and 34. A compression ring 710, designed to be inserted compressively to provide a fluid seal about support 706', provides for a seal and physical containment of valve 400.

As can be seen in FIGS. 30-32, a plunger valve 40 disposed in barrel 60' converts a single barrel syringe into a dual-chamber syringe 10", which provides closed system operation with a valve only opening when inserted into a female luer fitting. One skilled in medical syringe art well understands that, similarly, a single chamber syringe having a barrel 60' without a chamber dividing plunger valve would have similar closed system qualities. Critical parameters for building a model for a valve 400 can be calculated as provided hereafter. As an example, if a hole radius (R) is desired, a slit length (L) would be:

$$L = pi*(R)$$

However, as disclosed supra, for a given hole diameter, the slit length should be lengthened to account for lip separation 604 anomalies (See FIGS. 21-23). As an example, for a hole diameter of 0.055 inches, adding five percent to the length increases the slit length from 0.086 to 0.091.

Offsetting slit 440 (see FIG. 15) by twenty thousandths is preferred; however other offsetting amounts can be made within the scope of the instant invention. Once the slit length (hole size) and effective slit lengthening and offset are determined, it is recommended that ISO specifications be followed for calculating valve 400 design parameters. The following table I summarizes contemporary ISO specifications. It should be remembered that these specifications are provided for single chamber syringes.

TABLE I

Current Applicable ISO Specifications

|  | inches |
|---|---|
| Male luer length | .295 |
| Female luer length | .295 |
| Insertion variance | .159 |
| Maximum engagement length | .159 |
| Maximum insertion length | .226 |
| Male end diameter | .154 |
| Female insertion diameter | .159 |
| Male diameter at end | .156 |
| Variance of male fitting | .002 |
| Fitting taper | 3% |

For an elliptically formed valve, the only critical specifications are major and minor elliptical axes, insertion depth and associated fitting dimensions (diameter) at that depth and valve length. In the case of the current example, the desired parameters are 1. Fitting radius, i.e. at distal face 468 of inserted valve (r): 0.077 inches
2. Circumference at face 468 (C) 0.485
3. Slit offset (from major axis) (O) 0.020
4. Length of inside female fitting chord at slit offset (F) 0.149
5. Precompression length of valve at slit (P) 0.180

Given the above listed parameters, a value for a half major axis (A) can be calculated by the following:

The tangent (T) of an angle defined by a base of precompression length (P) and slit offset (O) is given by:

$$T = O/P$$

The angle ($\theta$) associated with "T" is:

$$\theta = \arctan(T)$$

An estimate for A is preferably calculated by:

$$A = F/(\cos \theta) = 0.093 \text{ inches}$$

Noting that calculated A, while close to a true value of the major axis is not exactly so, a value for the minor half axis (B) of the associated ellipse can be approximated from a known area (a) of the inner surface of the female fitting. Noting that desired area (a) is area of the fitting less area of hole which equals pi times R squared. Thus:

$$a = pi(r^2 - R^2) \text{ and an estimated value for B is estimated } B = a/(pi\ A) = 0.058 \text{ inches}$$

However, noting that both A and B are estimates, a check on the value of B by calculating circumference of the associated ellipse shows that a correction of +0.002 to B decreases an error in circumference comparing circumference of the associated ellipse to the circumference of the fitting to less than 0.2 percent. With A and B and slit length so determined, a cavity with a maximum width of 0.020 provides all of the necessary dimensions to fabricate a valve actuator 410 (see FIGS. 15 and 16) which is 0.100 inches long.

It should be noted that major axis (2A) being 0.186 inches long requires filleting 467 of the face 468 for facile insertion. Also, transition geometry within transition section 420 (See FIG. 15) should be linear to retain corresponding circumference between the associated female fitting and exterior surface of valve 400.

Systems Kit for Step Reduction

Reference is now made to FIG. 36 wherein a system 10 and a pre-filled female luer fitting syringe 800 are seen. Note that system 10 comprises a male luer fitting 810 and syringe 800 comprises a female luer fitting 820. Syringe 800 is a single chamber syringe pre-filled with a dose 830 destined to be dispensed into distal chamber 90 of system 10. It should be noted that syringe 800 may be specially made for storage of dose 830 (e.g. made from glass). Transferring dose 830 into chamber 90 of system 10 is accomplished by a single luer fitting connecting step thus eliminating other commonly used components, such as male/male connectors. By reducing system 10 filling to a single connection, problems, such as those associated with nosocomial infections, are reduced.

Conclusion

Inventions disclosed herein may be embodied in other specific forms without departing from the spirit or essential characteristics thereof. The present embodiments are therefore to be considered in all respects as illustrative and not restrictive, the scope of the inventions being indicated by the appended claims rather than by the foregoing description, and all changes which come within the meaning and range of equivalency of the claims are therefore intended to be embraced therein.

What is claimed and desired to be secured by Letters Patent is:

1. A dual-chamber syringe system comprising:
    a dual-chamber syringe comprising a medical syringe having a conventional hollow syringe barrel which comprises a hollow, substantially constant diameter inner wall, a distal end at which a distal chamber is filled and a proximal end which comprises a flanged opening sized and shaped for plunger introduction;
    said syringe also comprising a plunger rod and associated plunger tip which is disposed within said barrel for the purpose of displacing fluid therein;
    said dual-chamber syringe further comprising a plunger valve which is disposed to divide said barrel into two disparate chambers, a distal chamber which is disposed between said plunger valve and said distal end and a proximal chamber which is disposed between said plunger valve and said plunger tip, said proximal chamber being pre-filled with fluid which is dispensed only upon completion of a dispensing cycle of fluid from the distal chamber and said plunger valve being displaced only by force of fluid communicating with said plunger rod and associated plunger tip;
    said plunger valve comprising a valve plunger comprising an interfacing cylindrical outer wall which compressively wipes against said barrel inner wall to maintain disparity between the distal and proximal chambers and a fluid pathway tube between the proximal and distal chambers which is closed until fluid within the distal chamber is fully dispensed and further comprising integral structure disposed about said tube to compressively interface with said barrel inner wall to assure no fluid flow between said inner wall and said cylindrical outer wall and to keep said valve plunger from canting when displaced by only the liquid communication within said barrel thereby assuring maintenance of disparity between chambers when said plunger valve is closed and accuracy of measurement when said plunger valve is displaced and visually monitored for volume measurement;

said system comprising a visible indicator for valve and system readiness status for the purpose of avoiding use after inappropriate system handling due to a group of causes comprising tampering and inadvertent premature valve actuation;

said dual-chamber syringe further comprising a stop actuated at the end of a proximal chamber dispensing cycle which is effective in producing no refluxive flow; and wherein the syringe barrel includes a pattern of indicia provided on a surface thereof, the indicia comprising first and second sets of indicia overlapping and offset to clearly communicate volumetric measurement status for each distal and proximal chamber dispensing cycles, whereby the first indicia begins at the distal end of the syringe to correspond to a volume of fluid retained within the distal chamber and the second indicia begins a distance offset from the distal end corresponding to the size of the valve plunger in order to correspond to the volume of fluid retained within the proximal chamber.

2. A dual-chamber syringe system according to claim 1 wherein said plunger valve comprises a displaceable valve stem comprising a distal footing which is visible only when said plunger valve is closed to provide a closed valve indicator and a proximal plunger valve stem section which is visible only when the valve is opened to provide an indicator of an open valve thereby providing said visible indicator.

3. A dual-chamber syringe system according to claim 2 wherein said system comprises a removable sleeve affixed to said plunger rod to retard said rod from fully being displaced into said barrel and thereby impede premature displacement of said stem and resultant actuation of said plunger valve.

4. A dual-chamber syringe system according to claim 1 wherein said proximal chamber fluid comprises a liquid and a predetermined maximum volume of air which is not dispensed and said plunger valve pathway comprises an extended tube into a liquid only zone whereby only liquid is dispensed from the proximal chamber.

5. A dual-chamber syringe system according to claim 1 wherein said plunger rod comprises a shoulder disposed to provide a hard stop upon impact against said flanged opening to thereby deter refluxive flow at the end of a proximal chamber dispensing cycle.

6. A dual-chamber syringe system according to claim 1 comprising an additional measurement indicia patterned for measurement by a single displacing element.

7. A dual-chamber syringe system according to claim 6 wherein the displacing element is said plunger rod which comprises a pattern of indicia disposed thereon.

8. A dual-chamber syringe system according to claim 1 wherein said integral structure comprises solid wall construction perforated by at lest one of dead-ended hole, thereby providing space for collection of gas about said tube while providing support structure for said cylindrical outer wall.

9. A dual-chamber syringe system kit according to claim 1 further comprising a female luer syringe containing fluid to be drawn into said dual-chamber syringe, said dual-chamber syringe barrel comprising a male luer syringe such that fluid transfer is accomplished by a single male to female luer fitting connection.

10. A dual-chamber syringe system according to claim 1 wherein said barrel comprises a skeletal support for a tapered fitting valve.

* * * * *